(12) United States Patent
Wahl et al.

(10) Patent No.: US 12,023,259 B2
(45) Date of Patent: Jul. 2, 2024

(54) STERILE IMPLANT INSTRUMENTS AND KITS FOR FLEXIBLE JOINT IMPLANTS

(71) Applicant: IN2BONES USA, LLC, Memphis, TN (US)

(72) Inventors: Rebecca H. Wahl, Escondido, CA (US); Casey Chambers, Lafayette, CO (US)

(73) Assignee: In2Bones USA, LLC, Memphis, TN (US)

( * ) Notice: Subject to any disclaimer, the term of this patent is extended or adjusted under 35 U.S.C. 154(b) by 430 days.

(21) Appl. No.: 15/547,391

(22) PCT Filed: Mar. 18, 2016

(86) PCT No.: PCT/US2016/023184
§ 371 (c)(1),
(2) Date: Jul. 28, 2017

(87) PCT Pub. No.: WO2016/149635
PCT Pub. Date: Sep. 22, 2016

(65) Prior Publication Data
US 2018/0036142 A1 Feb. 8, 2018

Related U.S. Application Data

(60) Provisional application No. 62/135,263, filed on Mar. 19, 2015.

(51) Int. Cl.
*A61F 2/46* (2006.01)
*A61B 17/16* (2006.01)
(Continued)

(52) U.S. Cl.
CPC .......... *A61F 2/4603* (2013.01); *A61B 17/164* (2013.01); *A61B 17/1659* (2013.01);
(Continued)

(58) Field of Classification Search
CPC .... A61F 2/4603; A61F 2/4225; A61F 2/4657; A61B 17/1775; A61B 17/1782;
(Continued)

(56) References Cited

U.S. PATENT DOCUMENTS 2,576,235 A  11/1951  Nelson
2,961,755 A * 11/1960  Prince ..................... B25B 27/28
                                                       29/235

(Continued)

FOREIGN PATENT DOCUMENTS

WO      2005053753 A2    6/2005

OTHER PUBLICATIONS

International Search report for corresponding application PCT/US2016/023184 dated Aug. 5, 2016.

*Primary Examiner* — Ariana Zimbouski
*Assistant Examiner* — Christine L Nelson
(74) *Attorney, Agent, or Firm* — Rutan & Tucker LLP; Hani Z. Sayed

(57) ABSTRACT

Disclosed are sterile instruments and instrument kits for use in surgery, said instruments including a reamer assembly comprising a reamer depth stop and a reamer, a grommet placer instrument, and a sizing instrument for use in joint implant surgery. The invention also concerns a kit for use in joint implant surgery, comprising said reamer assembly, said grommet placer instrument, a wire guide, comprising a wire guide body, and a guide wire. A method for using one or more of the instruments and kit as described herein is also provided.

5 Claims, 19 Drawing Sheets

(51) Int. Cl.
 *A61B 17/17* (2006.01)
 *A61B 17/92* (2006.01)
 *A61F 2/30* (2006.01)
 *A61F 2/42* (2006.01)
 *A61B 90/00* (2016.01)

(52) U.S. Cl.
 CPC ...... *A61B 17/1682* (2013.01); *A61B 17/1686* (2013.01); *A61B 17/1775* (2016.11); *A61B 17/1782* (2016.11); *A61B 17/921* (2013.01); *A61F 2/30734* (2013.01); *A61F 2/4225* (2013.01); *A61F 2/4241* (2013.01); *A61F 2/4657* (2013.01); *A61B 2090/036* (2016.02); *A61F 2002/30069* (2013.01); *A61F 2002/30738* (2013.01); *A61F 2002/4228* (2013.01); *A61F 2002/4243* (2013.01); *A61F 2002/4658* (2013.01)

(58) Field of Classification Search
 CPC .............. A61B 17/1796; A61B 17/164; A61B 17/1659; A61B 17/1682; A61B 17/1686; A61B 17/921; A61B 2090/036
 See application file for complete search history.

(56) References Cited

U.S. PATENT DOCUMENTS

| | | | |
|---|---|---|---|
| 4,494,290 A | | 1/1985 | Rutledge |
| 4,939,960 A | | 7/1990 | Kinzli |
| 6,045,572 A | * | 4/2000 | Johnson ............ A61B 17/0401 |
| | | | 606/232 |
| 6,162,226 A | | 12/2000 | DeCarlo, Jr. et al. |
| 6,951,562 B2 | * | 10/2005 | Zwirnmann ....... A61B 17/1633 |
| | | | 606/80 |
| 7,141,074 B2 | | 11/2006 | Fanger et al. |
| 8,584,853 B2 | * | 11/2013 | Knight ............... A61B 17/0642 |
| | | | 206/439 |
| 2002/0133233 A1 | | 9/2002 | Blamey |
| 2013/0325019 A1 | | 12/2013 | Thomas et al. |
| 2013/0331850 A1 | | 12/2013 | Bojarski |

* cited by examiner

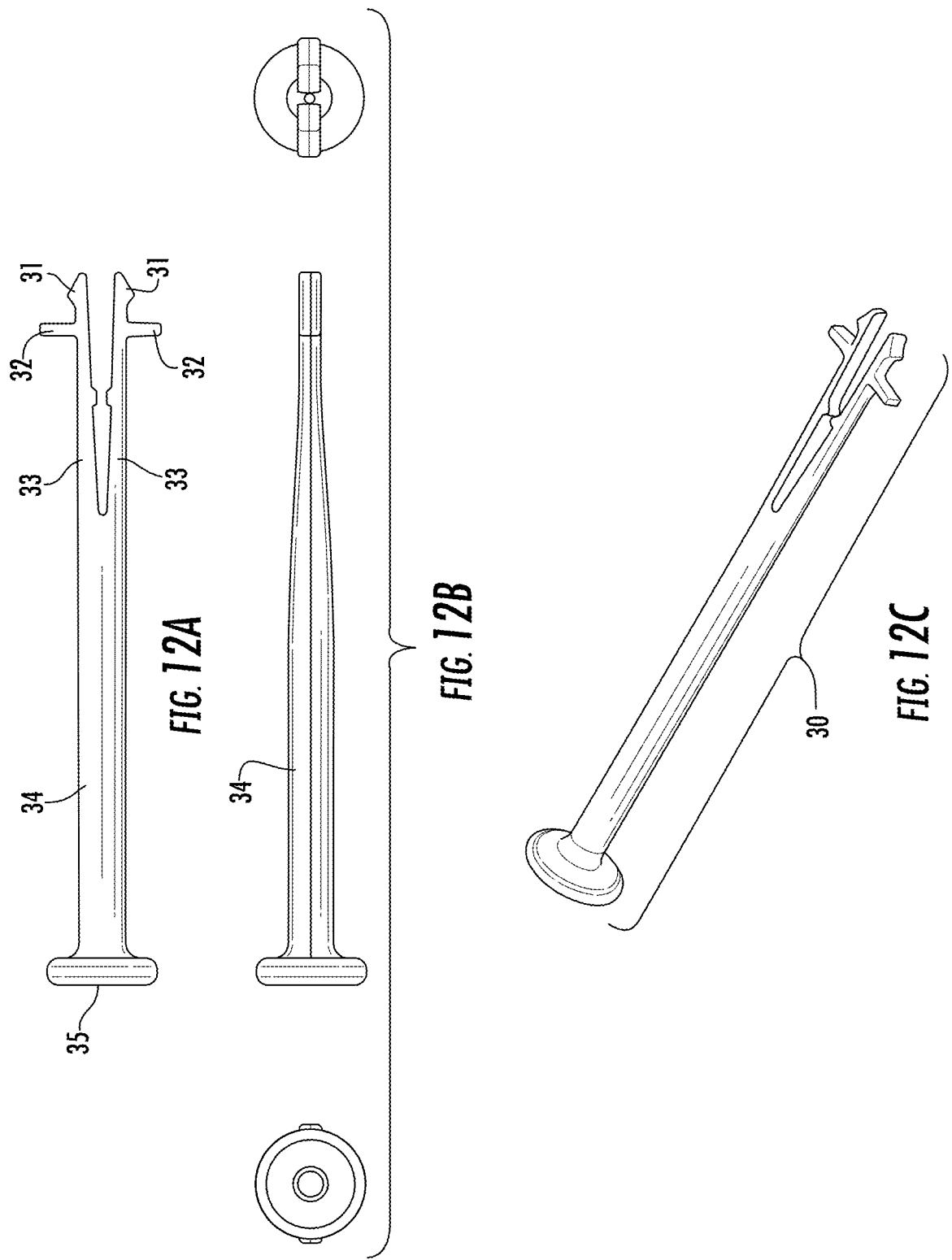

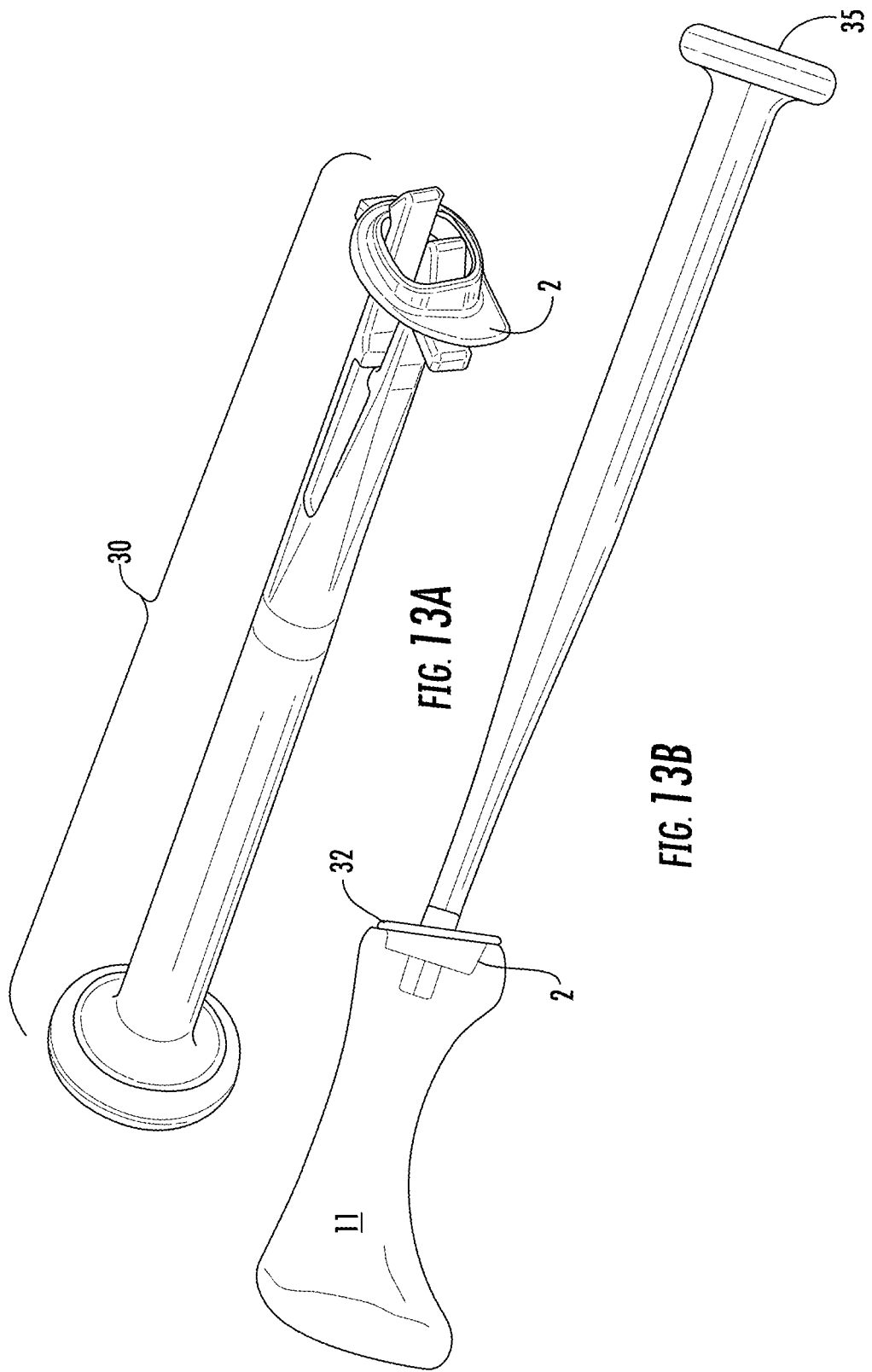

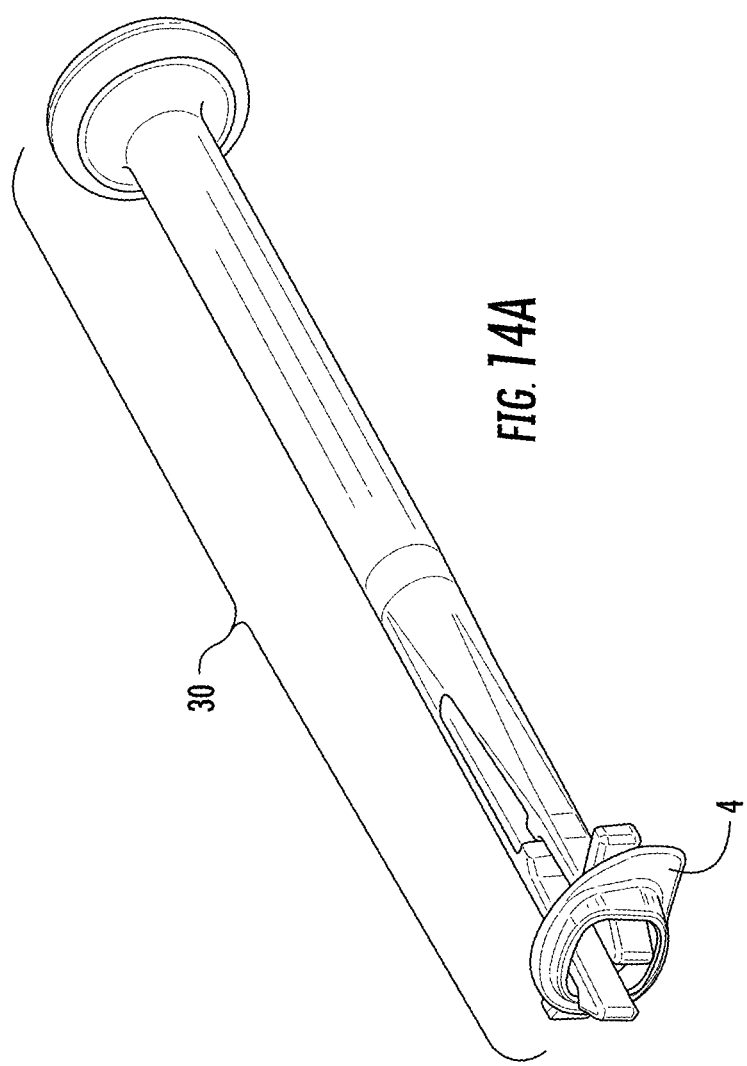
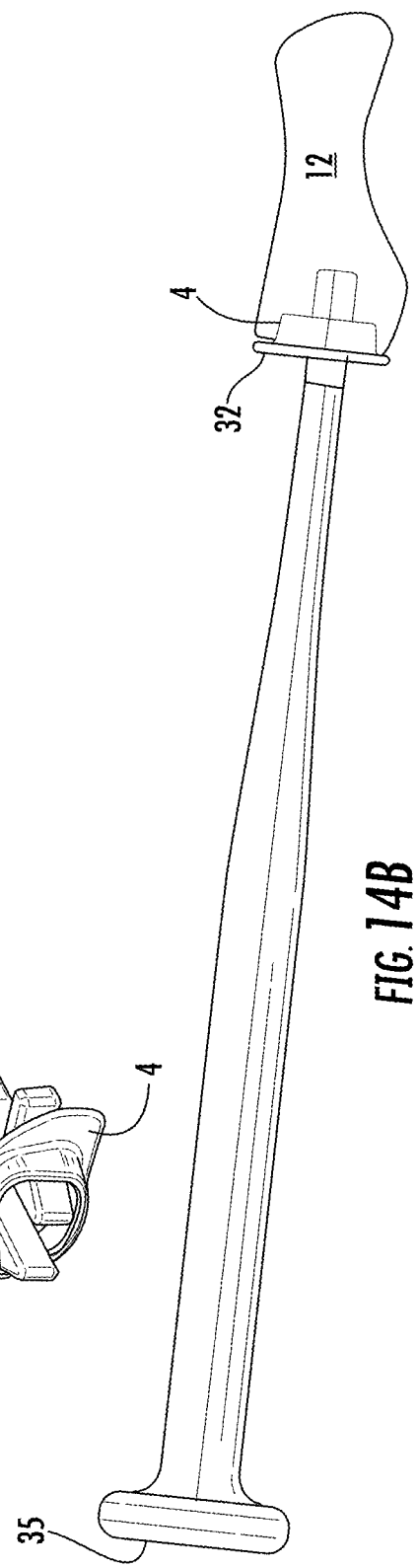
FIG. 14A
FIG. 14B

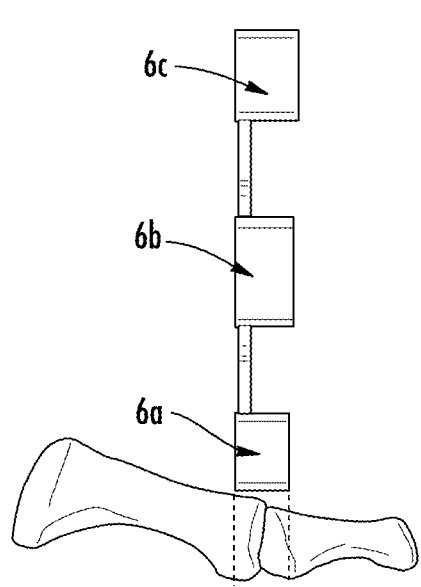
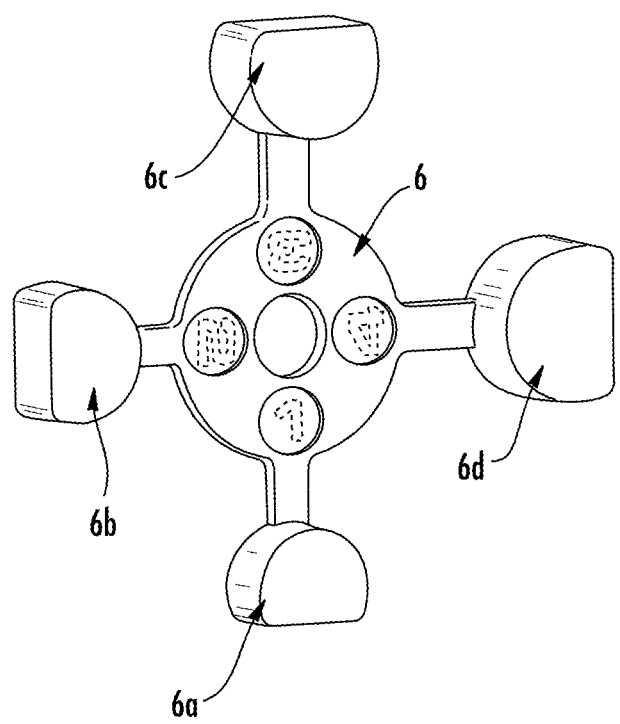
FIG. 15 A          FIG. 15 B

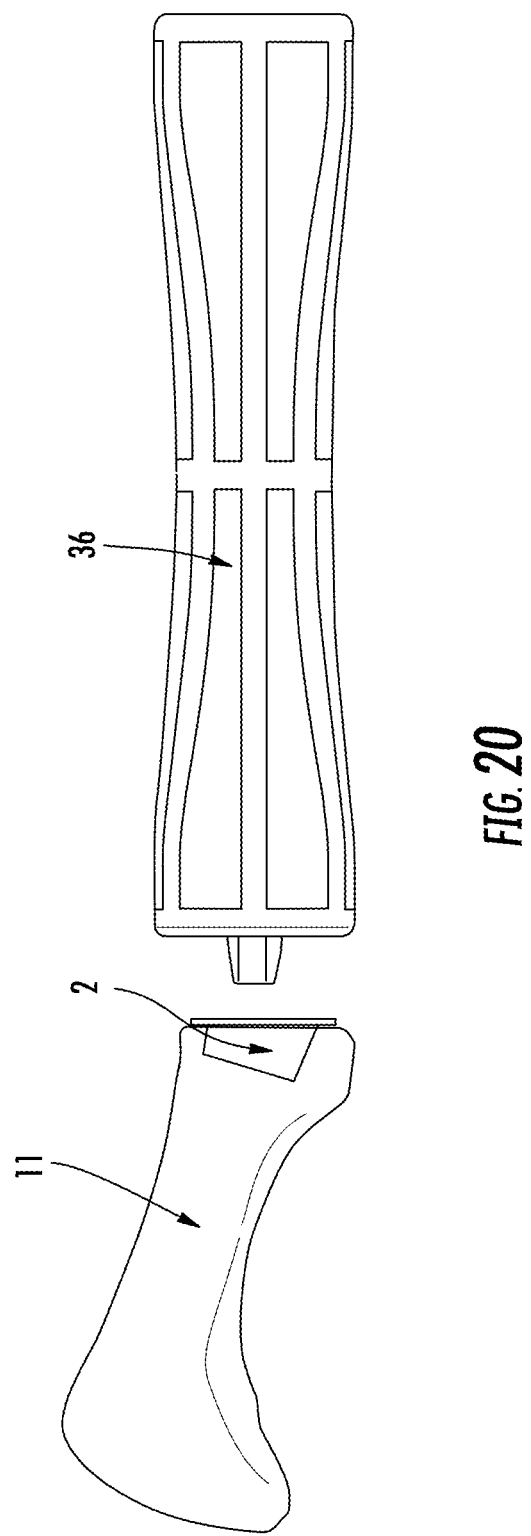

STERILE IMPLANT INSTRUMENTS AND KITS FOR FLEXIBLE JOINT IMPLANTS

FIELD OF THE INVENTION

The present invention concerns sterile instruments and sterile instrument kits for use in surgery as well as methods of use thereof. More specifically, the invention concerns single-use instruments for fitting and inserting an implant during arthroplasty, and associated surgical methods. The instruments, kits and surgical methods of the present invention are particularly useful for replacement of a joint of a digit by an implant, e.g., a toe or finger implant.

DISCUSSION AND COMPARISON WITH RELEVANT PRIOR ART

The instruments, kits and methods of the present invention is described with reference to the joint between a metatarsal bone and a proximal phalange of the foot in order to aid in understanding of the invention. An example of a toe implant for the joint between the metatarsal bone and the proximal phalange is described in U.S. Pat. No. 6,319,284, the entire content of which is hereby incorporated by reference herein. However, the scope of the instruments, kits and methods of the present invention is not intended to, and should not be construed to, be limited to said specific joint.

Conventional tools used in toe surgery require the surgeon to prepare the bones using free-hand techniques or to employ difficult to use cutting guides and poorly designed instruments that make it difficult to implant grommets successfully. Difficulty in seating grommets has led to a slow adoption rate of grommets despite theoretical reduction of silicone particulate that can cause synovitis and implant weakening. Recent studies demonstrate improved outcome of implants when used in conjunction with grommets. (Kanzaki et al. *J Orthop Surg* (*Hong* Kong). 2014 April; 22(1): 42-5; and S Jain, B Banerjee. Silastic flexible hinge implant arthroplasty of the great toe for hallux rigidus: A retrospective analysis. The Internet Journal of Orthopedic Surgery. 2007 Volume 9 Number 2).

The instruments and methods of the present invention provide advantages over conventional tools and methods used in surgical replacement of a joint by an implant. Aspects of the invention will be understood with reference to the following specification and drawings.

SUMMARY OF THE INVENTION

Disclosed are sterile instruments and instrument kits for use in surgery, said instruments including a reamer assembly comprising a reamer depth stop and a reamer, a grommet placer instrument, and a sizing instrument for use in joint implant surgery. The invention also concerns a kit for use in joint implant surgery, comprising said reamer assembly, said grommet placer instrument, a wire guide, comprising a wire guide body, and a guide wire. A method for using one or more of the instruments and kit as described herein is also provided.

BRIEF DESCRIPTION OF THE DRAWINGS

FIGS. 12A-12C illustrate a grommet placer instrument (also referred to herein as a grommet placer) according to an embodiment of the present invention. FIG. 12A illustrates the flexible split shafts in the open position. FIG. 12B illustrates the flexible split shafts in the closed position to allow placement of a grommet. FIG. 12C illustrates the flexible split shafts in the open position, shown in perspective view.

FIGS. 13A and 13B illustrate proximal grommet placement according to an embodiment of the present invention. FIG. 13A illustrates the flexible split shafts in the open position, with proximal grommet placed thereon. FIG. 13B illustrates the flexible split shafts in the closed position, with a proximal grommet placed thereon in the metatarsal bone.

FIGS. 14A and 14B illustrate distal grommet placement according to an embodiment of the present invention. FIG. 14A illustrates the flexible split shafts in the open position, with distal grommet placed thereon. FIG. 14B illustrates the flexible split shafts in the closed position, with a distal grommet placed thereon in the phalanx bone.

FIG. 15B shows an implant sizer according to an embodiment of the present invention. FIG. 15A shows said implant sizer positioned above the joint with dotted lines indicating bone resection width.

FIGS. 16B and 16C show alternative embodiments of FIGS. 3 and 4, respectively.

FIGS. 17A-17C show alternative embodiments of FIGS. 5-7, respectively.

FIG. 18B shows placement of the proximal grommet. FIG. 18C shows placement of the distal grommet. FIGS. 18B-18C show alternative embodiments of FIGS. 13B and 14B, respectively.

FIG. 20 shows an impactor according to an embodiment of the present invention.

DESCRIPTION OF THE PREFERRED EMBODIMENT

Figure 1A:
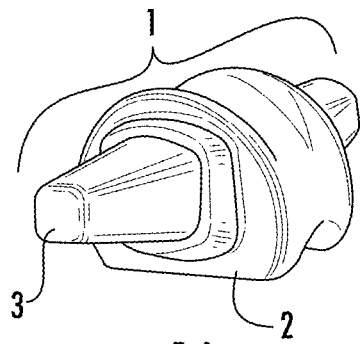
FIGS. 1A and 1B illustrate a perspective view and an elevation view, respectively, of a flexible hinge implant with grommets.

The present invention concerns sterile instruments and instrument kits for use in surgery. More specifically, the invention concerns single-use, cannulated instrumentation and kits containing the same for fitting and inserting an implant during arthroplasty, and associated surgical methods.

The instruments, kits and methods of the invention described herein are useful for arthroplasty during which a joint is replaced by an implant, e.g., a sterile, polymer/silicone, flexible hinge toe implant with grommets. The kit of the present invention may comprise one or more of: a sizing instrument, a wire guide, a guide wire (also called a guide pin), a cannulated reamer having an adjustable reamer depth stop for proximal and distal reaming depths and a channel to receive the guide wire, and a grommet placer/impactor for implanting the grommet. The kit may also include silicone flexible hinge toe implants and grommets. Trial implants and/or a proximal and distal broach for cutting an opening in the bone, which opening being shaped and sized to receive a grommet can optionally be included. Preferably, the instruments described herein are sterile and/or disposable.

The present invention further provides a surgical method for using the instrument kit including a reamer and corresponding reamer depth stop, and grommet placer, and optionally the broach as described herein. In an embodiment, this method comprises the steps of preparing of the joint and bone, selecting the size of the implant using a sizing instrument (e.g., a sizing wheel), preparing the intramedullary canal of the metatarsal bone by placing a guide wire into the intramedullary canal of the metatarsal bone using a wire guide, removing the wire guide and driving the reamer over the guide wire to prepare a first canal having a pre-set proximal depth, removing the reamer and guide wire, optionally inserting the cutting tip of a broach into the first canal, optionally impacting the broach to cut an opening sized and shaped to receive a proximal grommet, and implanting the proximal grommet into the metatarsal bone using a grommet placer; and performing analogous steps on the opposite bone of the joint, in this case, the proximal phalanx. Specifically, preparing the intramedullary canal of the proximal phalanx by placing a guide wire into the intramedullary canal of the proximal phalanx using a wire guide, removing the wire guide and driving the reamer over the guide wire to prepare a second canal having a pre-set distal depth, removing the reamer and guide wire, optionally inserting the cutting tip of a broach into the second canal, optionally impacting the broach to cut an opening sized and shaped to receive a distal grommet, and implanting the distal grommet into the proximal phalanx using the grommet placer.

With reference to FIGS. 1-20, two methods according to the present invention are described below. These exemplary methods are set forth to aid in an understanding of the subject matter but are not intended to, and should not be construed to, limit in any way the claims which follow thereafter. Further, in these figures, like or corresponding elements presented in different drawing figures are identified using the same reference numeral.

Figure 1B:
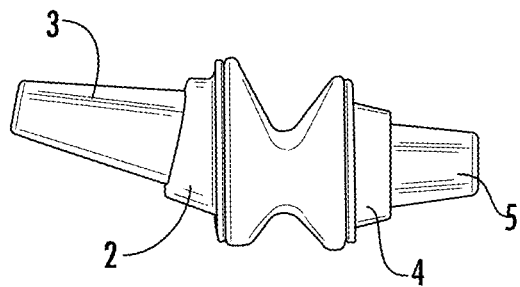

In FIG. 1, a flexible hinge implant (1) is illustrated in perspective in FIGS. 1A and 1n elevation in FIG. 1B. A proximal grommet (2) is shown on a proximal stem (3) and a distal grommet (4) is shown on distal stem (5). Trial implants are sized and shaped the same as the flexible hinge implant (1).

The present invention provides a reamer assembly for use in joint implant surgery, comprising: a) a reamer depth stop (15) having a body and at least two flexible tongs (19) extending from the body; and b) a reamer (14) comprising: (i) a reamer shaft (16) comprising a proximal end and a distal end, (ii) a cutting tip (22) located at the distal end of the reamer shaft (16), (iii) a hollow channel (23) within and extending through the cutting tip (22) and the reamer shaft (16), and (iv) at least two grooves located on the reamer shaft, representing a proximal stop position (17) and a distal stop position (18); wherein the at least two flexible tongs (19) are shaped and configured to snap in place at the proximal stop position (17) and then the distal stop position (18) when the reamer depth stop (15) is slid on to the reamer (14) in a direction from the proximal end to the distal end.

In an embodiment, the reamer (14) comprises an indent (21) and a flattened portion (20) located near the proximal end of the reamer (14), said indent (21) and flattened portion (20) configured and shaped to facilitate quick connect attachment to a driving tool.

Figure 5:
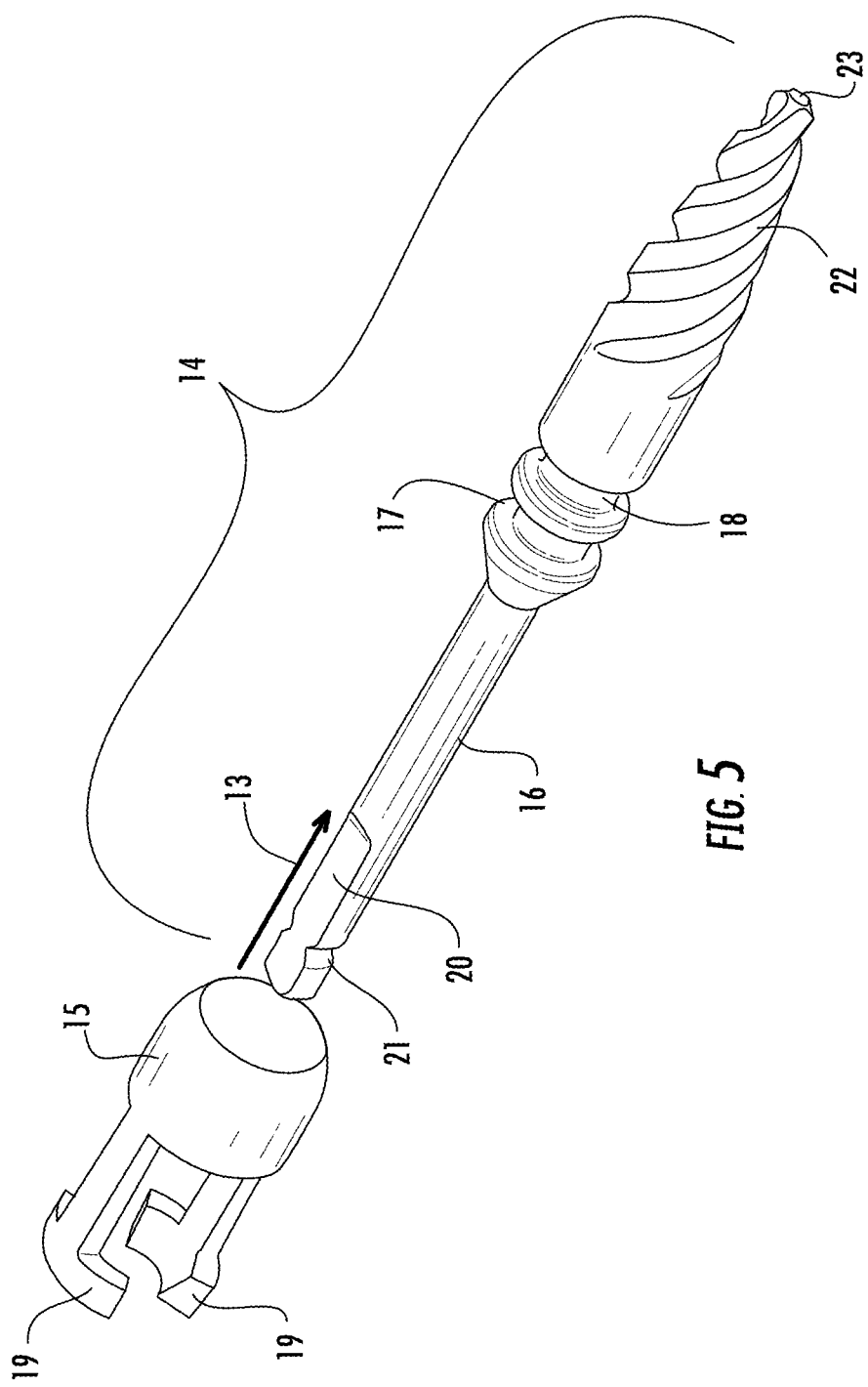
FIG. 5 is an exploded perspective view of a reamer assembly according to an embodiment of the present invention, including a reamer depth stop and a reamer, showing the direction which the reamer depth stop can be slid onto the reamer.
Figure 6:
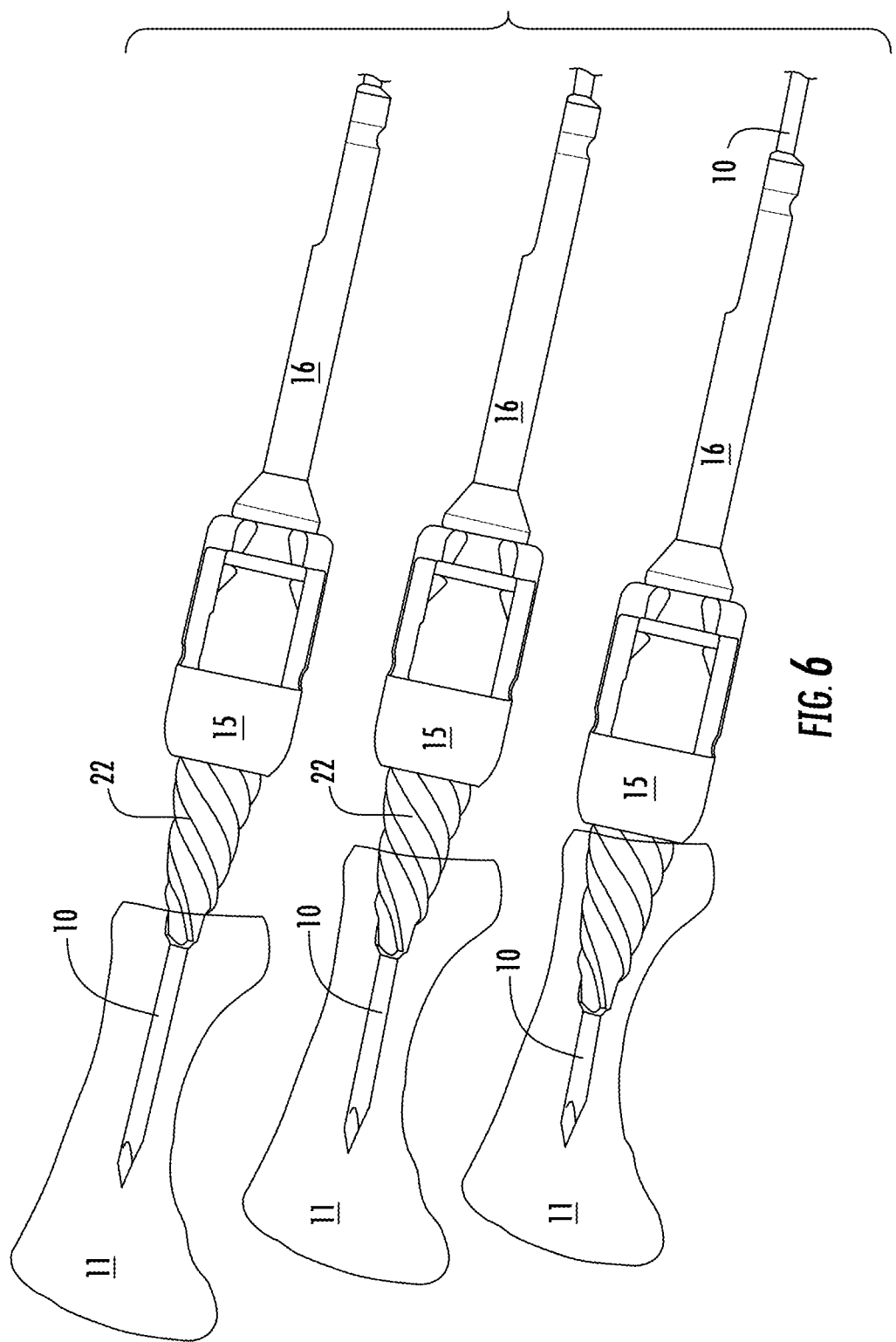
FIG. 6 shows positioning of the reamer and reamer depth stop during proximal reaming/drilling according to an embodiment of the present invention, and illustrates proximal reaming of the metatarsal bone using the instruments described herein.
Figure 7A:
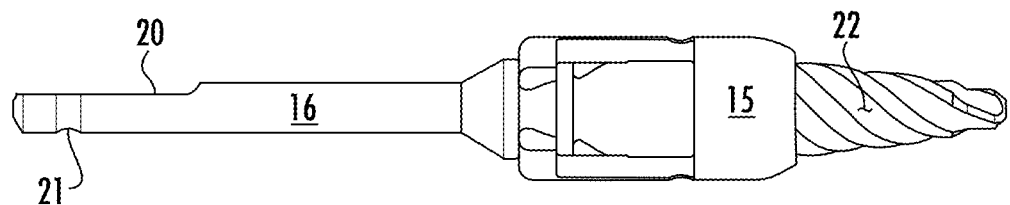
FIGS. 7A-7D show the reamer and sliding direction of the reamer depth stop (forward) according to an embodiment of the present invention, with illustrations of the reamer depth stop in the proximal drilling position (FIG. 7A for side elevation view, FIG. 7C for perspective view) and the reamer depth stop in the distal drilling position (FIG. 7B for side elevation view, FIG. 7D for perspective view).
Figure 7B:
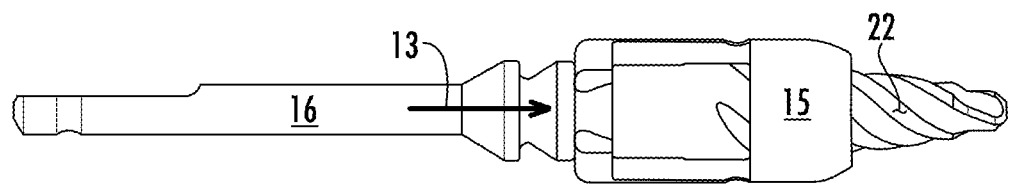
Figures 7C, 7D:
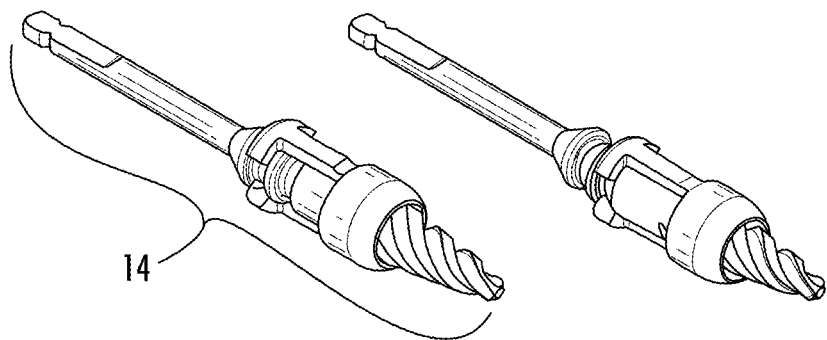
Figure 8:
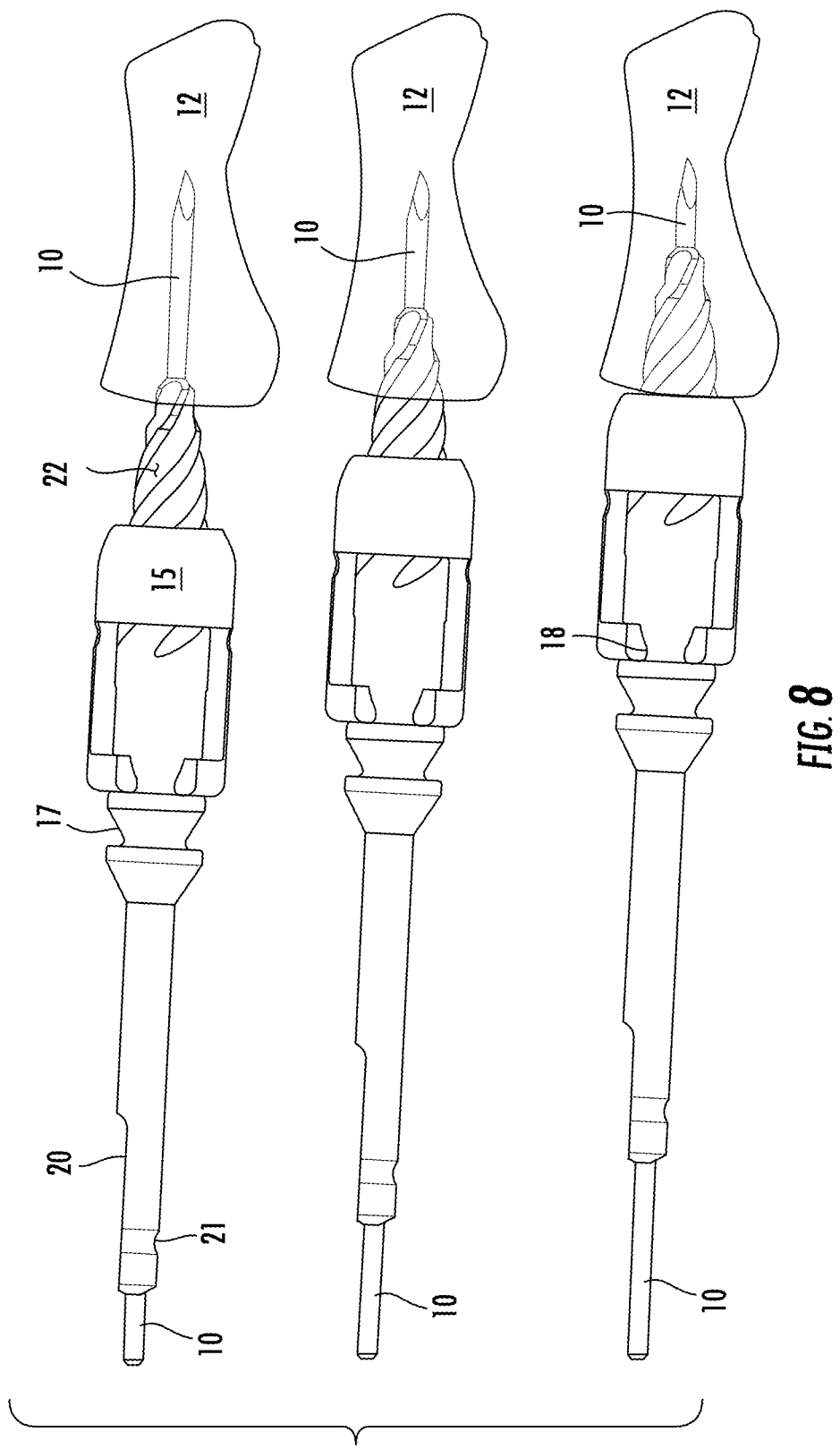
FIG. 8 illustrates distal reaming of the proximal phalanx according to an embodiment of the present invention.
Figure 9A:
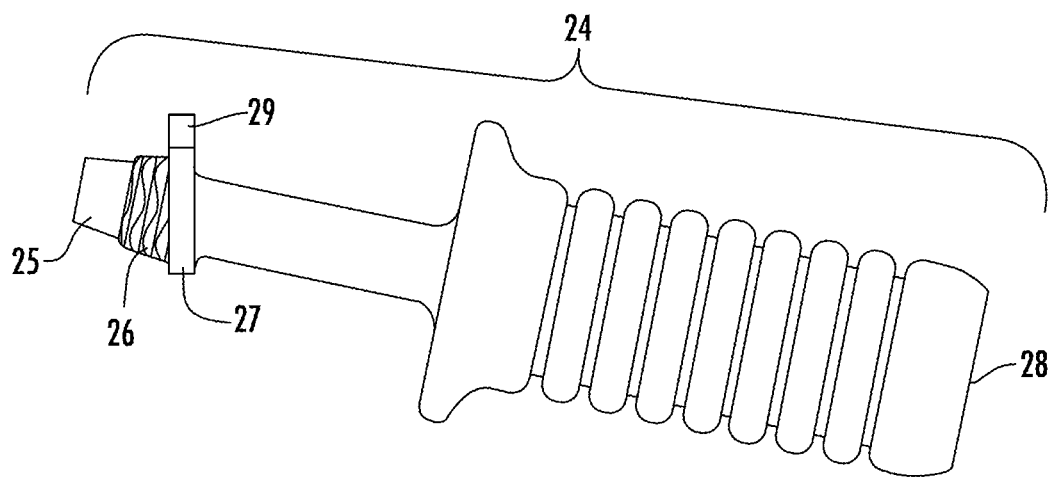
FIGS. 9A and 9B are an elevation view (FIG. 9A) and a perspective view (FIG. 9B) of a broach according to an embodiment of the present invention.
Figure 9B:
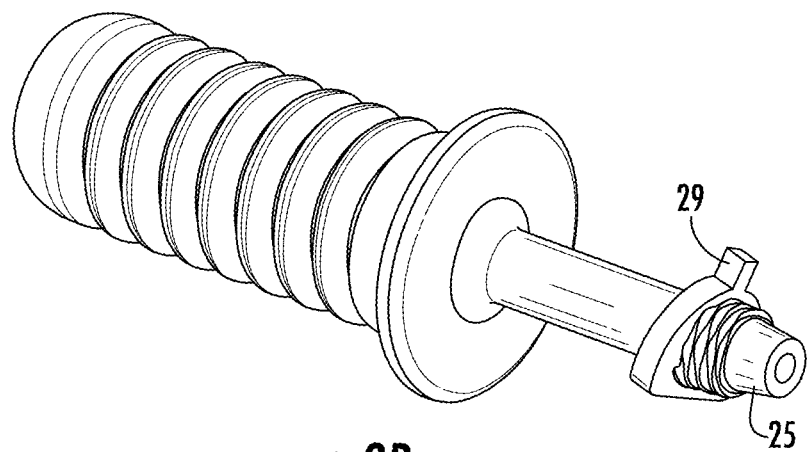

An exploded perspective view of the reamer (14) is shown in FIG. 5. Arrow (13) shows the direction for sliding the reamer stop (15), also referred to herein as "reamer depth stop", along the shaft (16). When the reamer stop (15) is in the proximal position, flexible tongs (19) snap in place at the proximal stop (17). When the reamer stop (15) is in the distal position, flexible tongs (19) snap in place at distal stop (18). These positions are illustrated in FIGS. 6-8. Preferably spring action of the design enables the reamer stop (15) to click into place in the proximal stop (17) or the distal stop (18). The shape of the tongs (19) discourages slippage out of the stops (17) or (18) when pushed toward the proximal end of the reamer (14). The shape also allows release from the stops (17) or (18) when pushing the reamer stop (15) forward towards the distal tip of reamer (14). The reamer shaft (16) has a flattened portion (20) and an indent (21) for a quick connect attachment to a driving tool. Cutting tip (22) is provided at the distal end of the reamer (14) and channel (23) extends through the cutting tip (22) and the shaft (16) for receiving the guide wire (10).

Figure 17A:
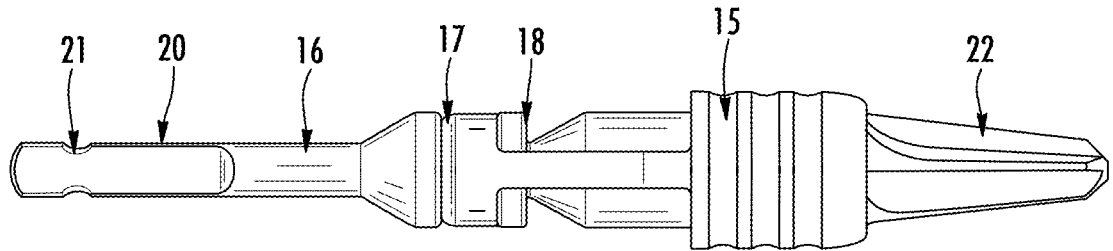
FIGS. 17A and 17B show an example of the cannulated reamer (FIG. 17A) and its positioning in the metatarstal bone during the reaming process (FIG. 17B). Positioning of the cannulated reamer in the phalanx bone during the reaming process is shown in FIG. 17C.
Figure 17B:
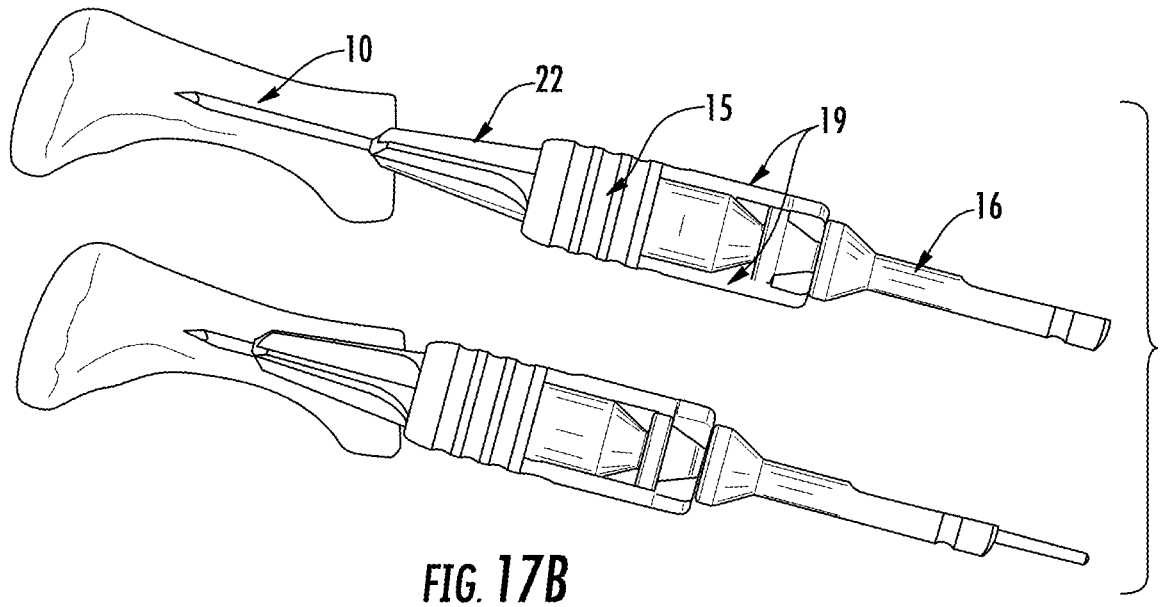
Figure 17C:
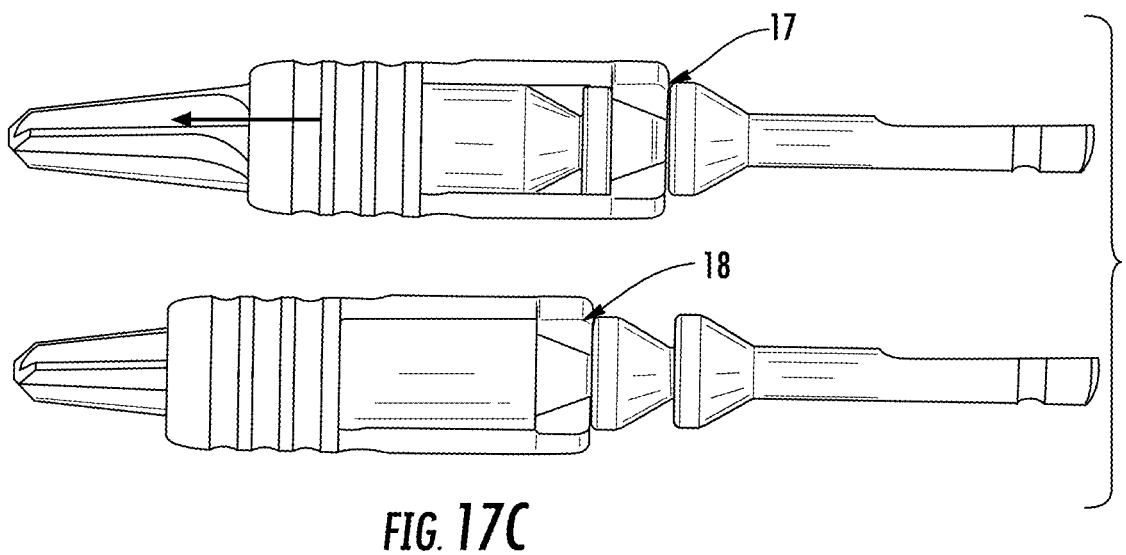

FIG. 6 shows the reamer at increasing depths in the metatarsal bone (11) and FIG. 8 shows the reamer at increasing depths in the proximal phalanx (12). FIG. 7 illustrates the reamer (14) with the reamer stop (15) in the proximal drilling position (FIGS. 7A and 7C) and also illustrates the reamer (14) with the reamer stop (15) in the distal drilling position (FIGS. 7B and 7D). The cutting tips of FIGS. 5-7 have a helical profile. In contrast, FIGS. 17A-17C show alternative embodiments where the cutting tip has a more smooth and straight line profile.

The present invention also provides a grommet placer instrument (30) for use in joint implant surgery, comprising a) a grommet placer shaft (34) comprising a proximal end and a distal end; b) a grommet placer head (35) located on the proximal end of the grommet placer shaft; c) at least two flexible split shafts (33) located on the distal end of the grommet placer shaft (34); d) a grommet stop (32) extending from each of the at least two flexible split shafts (33); and e) a grommet clip (31) extending from each of the at least two flexible split shafts (33); wherein, the grommet stops (32) are shaped and configured to prevent a grommet (2 or 4) placed on the grommet placer instrument (30) from sliding proximally on the grommet placer shaft (34), and the grommet clips (31) are shaped and configured to prevent the grommet (2 or 4) from falling off tips of the grommet placer.

Exemplary grommet placer instruments (30) are illustrated in FIGS. 12-14 and 18A. FIG. 12A is a top elevation view, FIG. 12B is a side elevation view and FIG. 12C is a perspective view. The grommet placer (30) has a grommet clip (31) and a grommet stop (32) on each flexible split shaft (33). Grommet placer shaft (34) extends to grommet placer head (35). The head (35) is tapped or pushed in the direction of the bone in order to install a grommet, preferably a metal grommet, in the bone. This design allows a grommet to be held in place on the instrument while being inserted. When the grommet is fully seated it is released from the grommet placer. Grommet stops (32) keep the grommet from sliding proximally on the grommet placer shaft (34). Grommet clips (31) keep the grommet from falling off the tip of the grommet placer (30). The grommet placer shown in FIG. 18A has a different grommet stop (32) design from that shown in FIGS. 12-14. Specifically, the grommet stop (32) is has a wider area for fingertip actuation, to compress the flexible split shafts (33) together for inserting and removing the grommet (2 or 4).

While in a preferable embodiment the grommet placer (30) has two flexible split shafts (33), a grommet placer (30) having more than two flexible split shafts (33) is also within the scope of the present invention. Where there are more than two flexible split shafts (33), it is possible that the number of grommet clips (31) and grommet stops (32) are less than the number of flexible split shafts (33), such that not all flexible split shafts (33) have grommet clips (31) and grommet stops (32) extending therefrom. For example, if four flexible split shafts (33) are present, it is possible that only two of said flexible split shafts (33) would have a grommet clip (31) and a grommet stop (32) extending therefrom. Alternatively, it is possible that two of the flexible split shafts (33) have grommet clips (31) extending therefrom while the other two flexible split shafts (33) have grommet stops (32) extending therefrom. The goal of the configuration of the flexible split shafts (33), grommet clips (1) and grommet stops (32) is to prevent the grommet placed on the grommet placer (30) from sliding proximally on the grommet placer shaft (34), and from falling off tips of the grommet placer instrument (30).

Figure 18A:
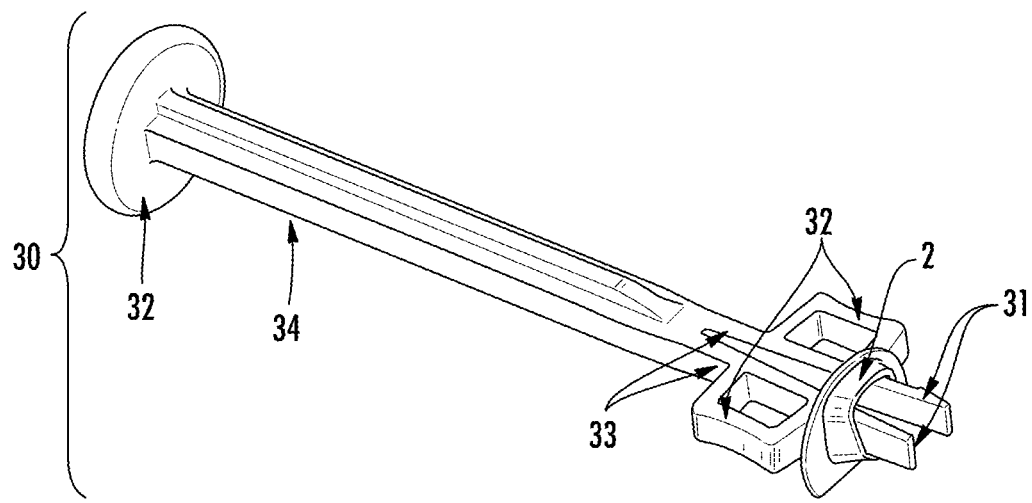
FIGS. 18A-18C show an example of the grommet placer having a grommet placed thereon (FIG. 18A), and use of said grommet placer to place a grommet in the bone.
Figure 18B:
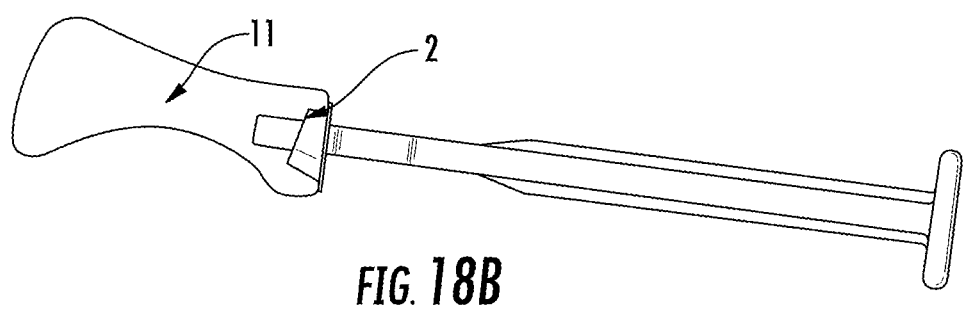
Figure 18C:
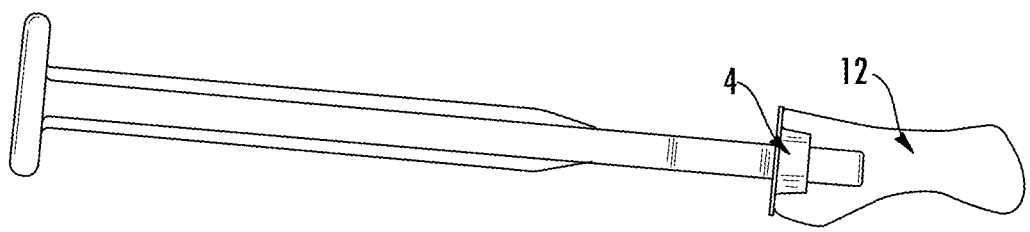

In FIG. 13A, a proximal grommet (2) is shown on grommet placer (30). FIG. 13B shows the proximal grommet (2) placed in the metatarsal bone (11). In FIG. 14A, a distal grommet (4) is shown on grommet placer (30). FIG. 14B shows the distal grommet (4) placed in the proximal phalanx (12). Similarly, FIG. 18B shows placement of proximal grommet (2) in the metatarsal bone (11) while FIG. 18C shows placement of distal grommet (4) in the proximal phalanx (12).

Figure 2:
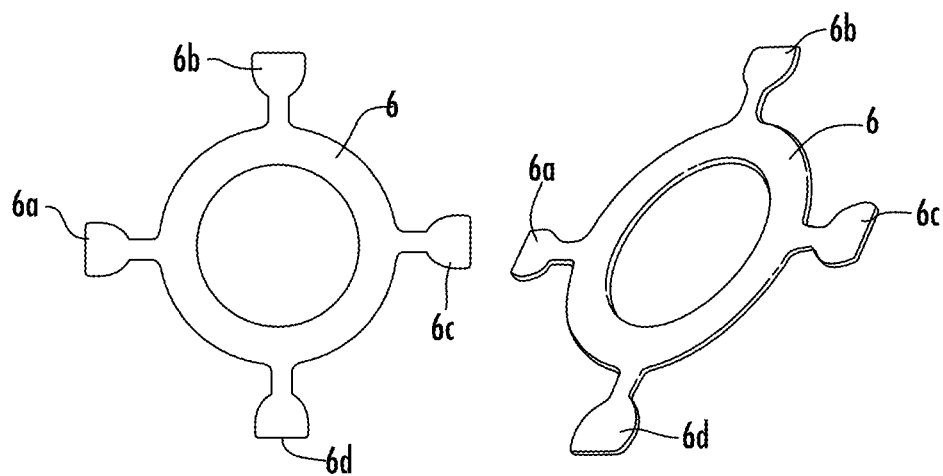
FIG. 2 illustrates a sizing instrument used for selecting the size of the implant according to an embodiment of the present invention.

The present invention also provides a sizing instrument (6) for use in joint implant surgery, comprising a) a central body; and b) at least four size guides (6a, 6b, 6c and 6e) extending from the central body, each size guide comprising a size guide head, each size guide head being of a different size from each of the other size guide heads. In one embodiment, each size head has a different thickness from each of the other size guide heads. Two views of sizing instrument (6) (e.g., a sizing wheel) are shown in FIG. 2 with size guides 6a, 6b, 6c and 6d. An alternative embodiment of the sizing instrument is shown in FIG. 15B, with size guides 6a, 6b, 6c and 6d. In FIG. 15, the thickness of the size guide heads vary.

The present invention also provides a kit for use in joint implant surgery, comprising: a) the reamer assembly as described herein, b) a grommet placer instrument as described herein, c) a wire guide (7), comprising a wire guide body, a proximal guide (8) located on a first end of the wire guide body, and a distal guide (9) located on a second end of the wire guide body, wherein the first and second ends are opposite ends of the wire guide body; and d) a guide wire (10), comprising an elongated guide wire body and a needle head located on one end of the elongated guide wire body.

In one embodiment of the kit, components a)-d) are provided in a sterile package. In another embodiment, the kit further comprises the sizing instrument as described herein, wherein the sizing instrument is optionally provided in a sterile package separate from components a)-d). In another embodiment, the kit further comprises a joint implant, wherein the joint implant is optionally provided in a sterile package separate from components a)-d). In another embodiment, the kit further comprises a broach (See, e.g., FIGS. 9A, 9B, and 10). In yet another embodiment, the kit further comprise a grommet impactor (see, e.g., FIG. 20), also referred to herein as the "impactor".

Figure 3:
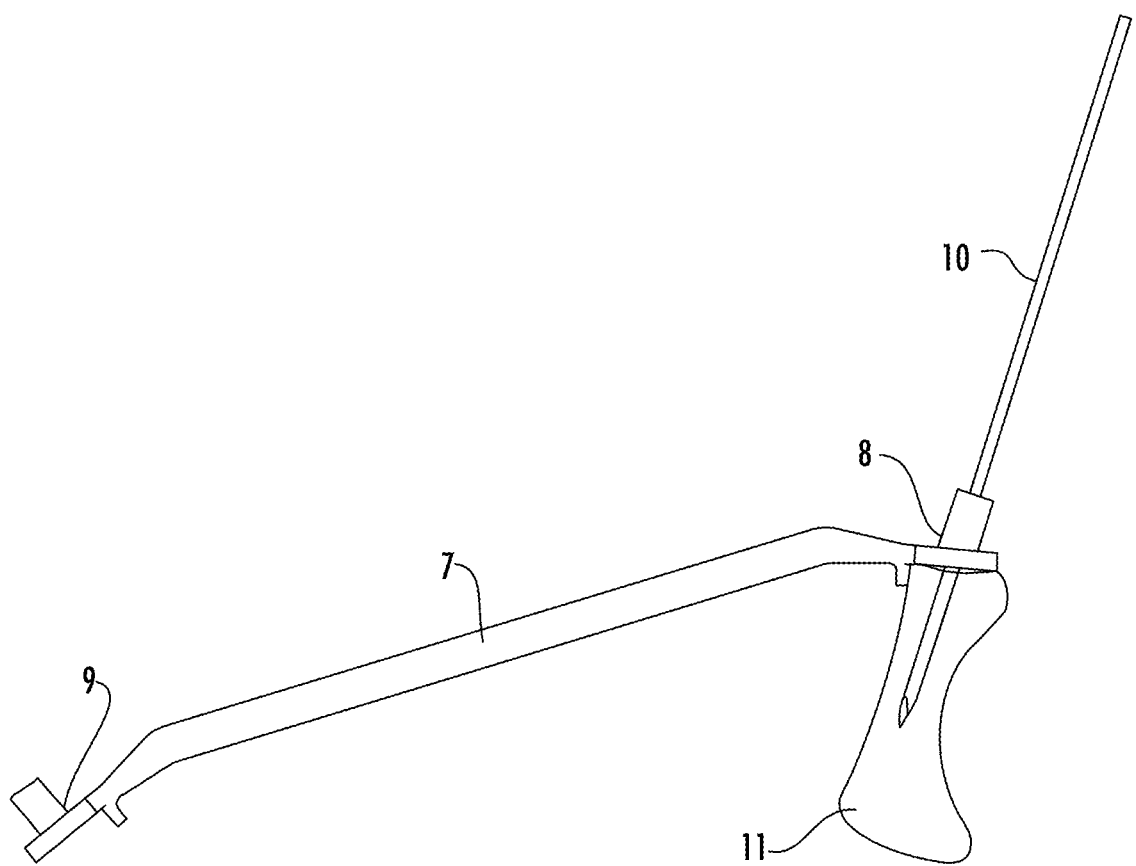
FIG. 3 shows a wire guide, a guide wire (or guide pin) and proximal placement of the guide wire in the intramedullary canal of a resected metatarsal bone.
Figure 4:
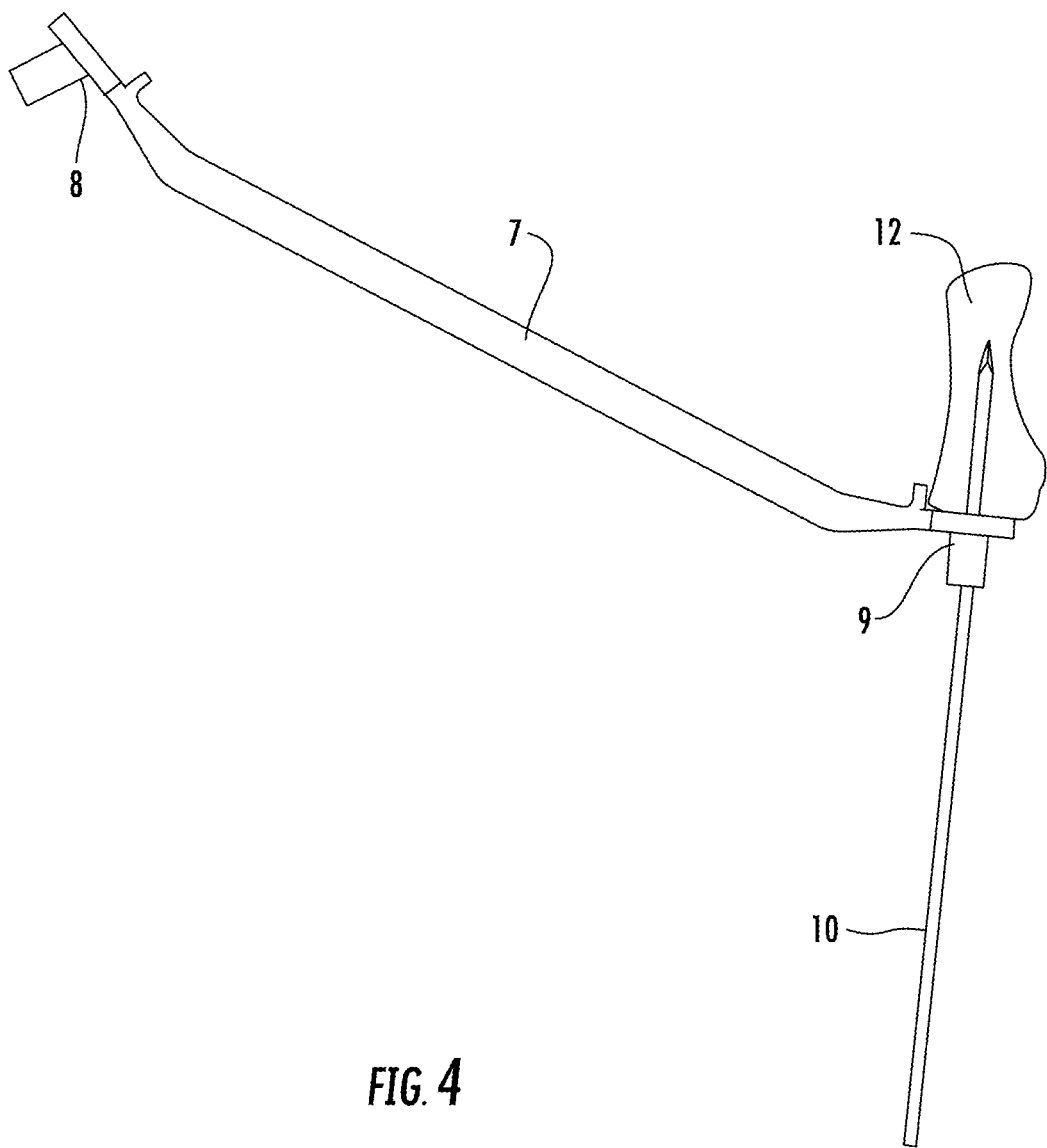
FIG. 4 shows a wire guide, a guide wire and distal placement of the guide wire in the intramedullary canal of the proximal phalanx.
Figure 16A:
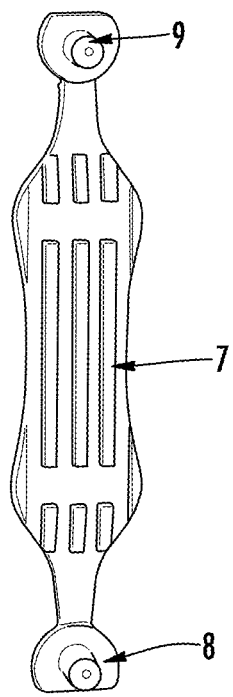
FIGS. 16A and 16B show an example of the wire guide (FIG. 16A) and its positioning against the metatarstal bone (FIG. 16B). Positioning of the wire guide against the phalanx bone is shown in FIG. 16C.
Figure 16B:
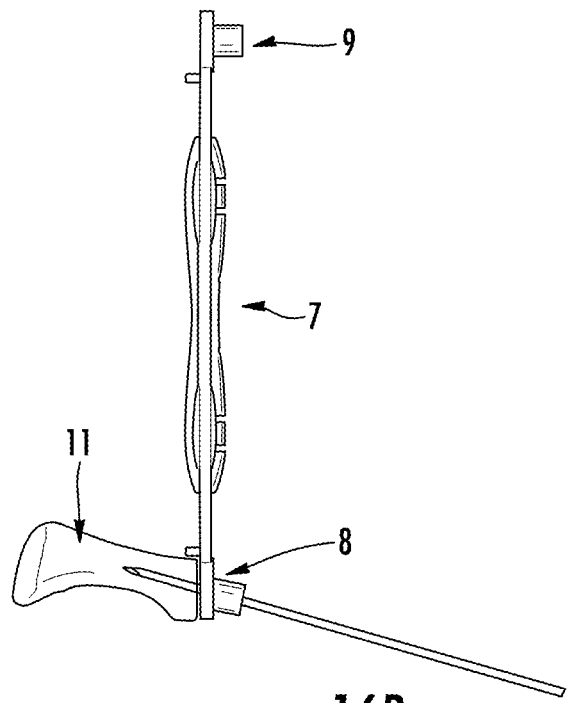
Figure 16C:
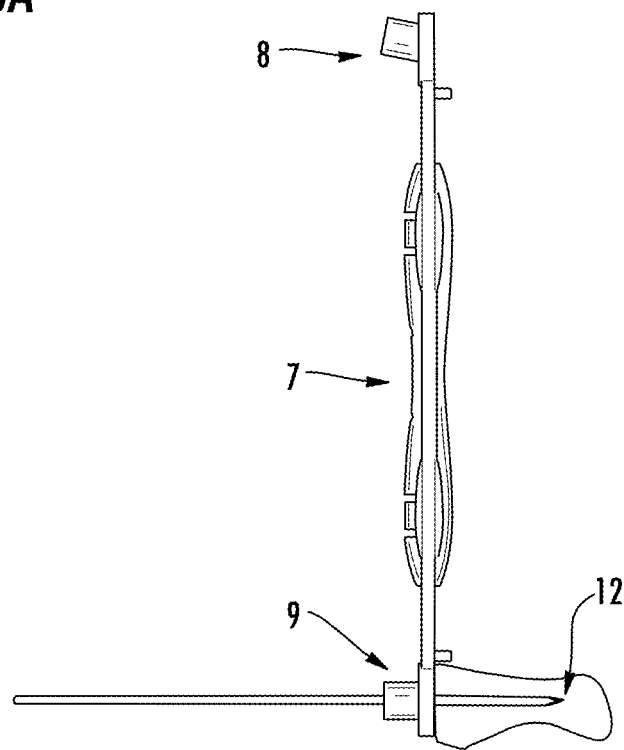

Wire guide (7) is shown in FIGS. 3, 16A and 16B as having a proximal guide (8) and a distal guide (9). Guide wire (10) is shown inserted into the intramedullary canal of a resected metatarsal bone (11). The bone (11) in FIGS. 3 and 16B is shown as translucent for illustration purposes as are the other bones in the appended drawings. The same wire guide and wire elements are shown in FIGS. 4 and 16C wherein the guide wire (10) is shown inserted into the intramedullary canal of a resected proximal phalanx (12).

The present invention also provides a method of performing joint implant surgery, comprising the steps: a) prepare a first bone of the joint to be replaced by making at least one incision in the first bone; b) selecting an appropriate-sized implant and appropriate-sized instruments based on a comparison between a sizing instrument and the first bone, wherein said instruments include one or more of a wire guide, a guide wire, a reamer assembly comprising a reamer and a reamer depth stop, a broach, a trial implant, a grommet placer instrument, at least two grommets, and a joint implant; c) positioning the wire guide against the first bone and drive the guide wire through said wire guide into the first bone, then removing wire guide; d) driving the reamer over the guide wire, thereby reaming the first bone until the reamer depth stop snap in place at an appropriate depth stop position, then removing the reamer and the guide wire; d) repeating steps a)-d) for a second bone of the joint to be replaced; f) implanting the at least two grommets in the first and the second bone, respectively; and g) implanting the joint implant.

In one embodiment, the method further comprises a step d)1) after step d) and before step e), of broaching the first bone. In another embodiment, in step e), step d)1) is performed on the second bone. In another embodiment, the method further comprise a step of e)1) after step e) and before step f) of checking joint preparation with the trial implant. In yet another embodiment, step f) is performed using the grommet placer instrument (30).

The broach (24) in FIG. 9 has a guide tip (25) for insertion into the reamed end of the bone. A toothed cutting ring (26) is provided adjacent a broach stop (27). The broach (24) is tapped with a hammer at strike plate (28) to cause toothed cutting ring (26) to cut the bone in an optimal site and shape that will receive a grommet. Broach stop (27) stops the toothed cutting ring (26) at the appropriate depth. Site guide (or orientation indicator) (29) assists the surgeon in maintaining proper orientation during impaction.

Figure 10:
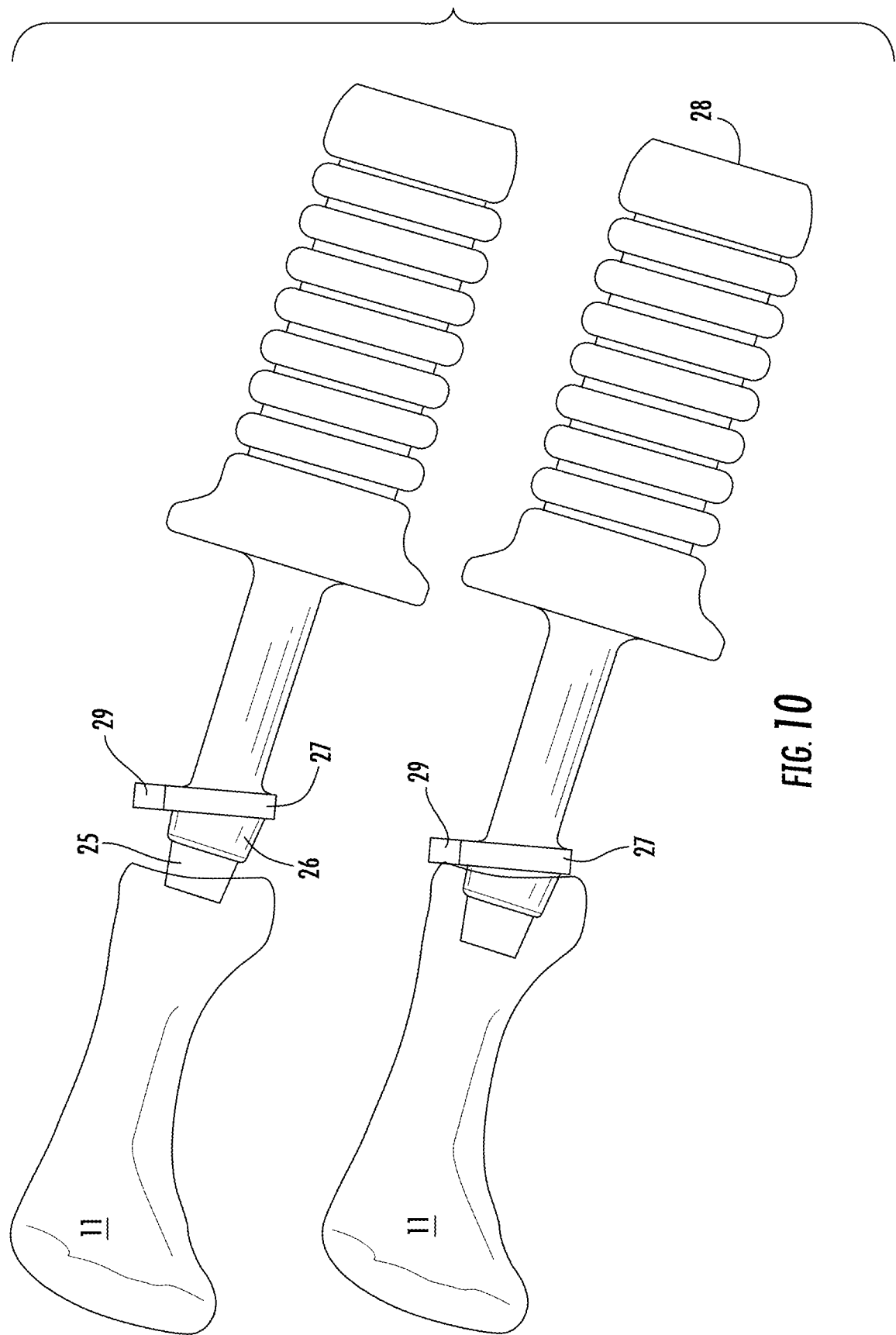
FIG. 10 illustrates proximal broaching of the metatarsal bone according to an embodiment of the present invention.
Figure 11:
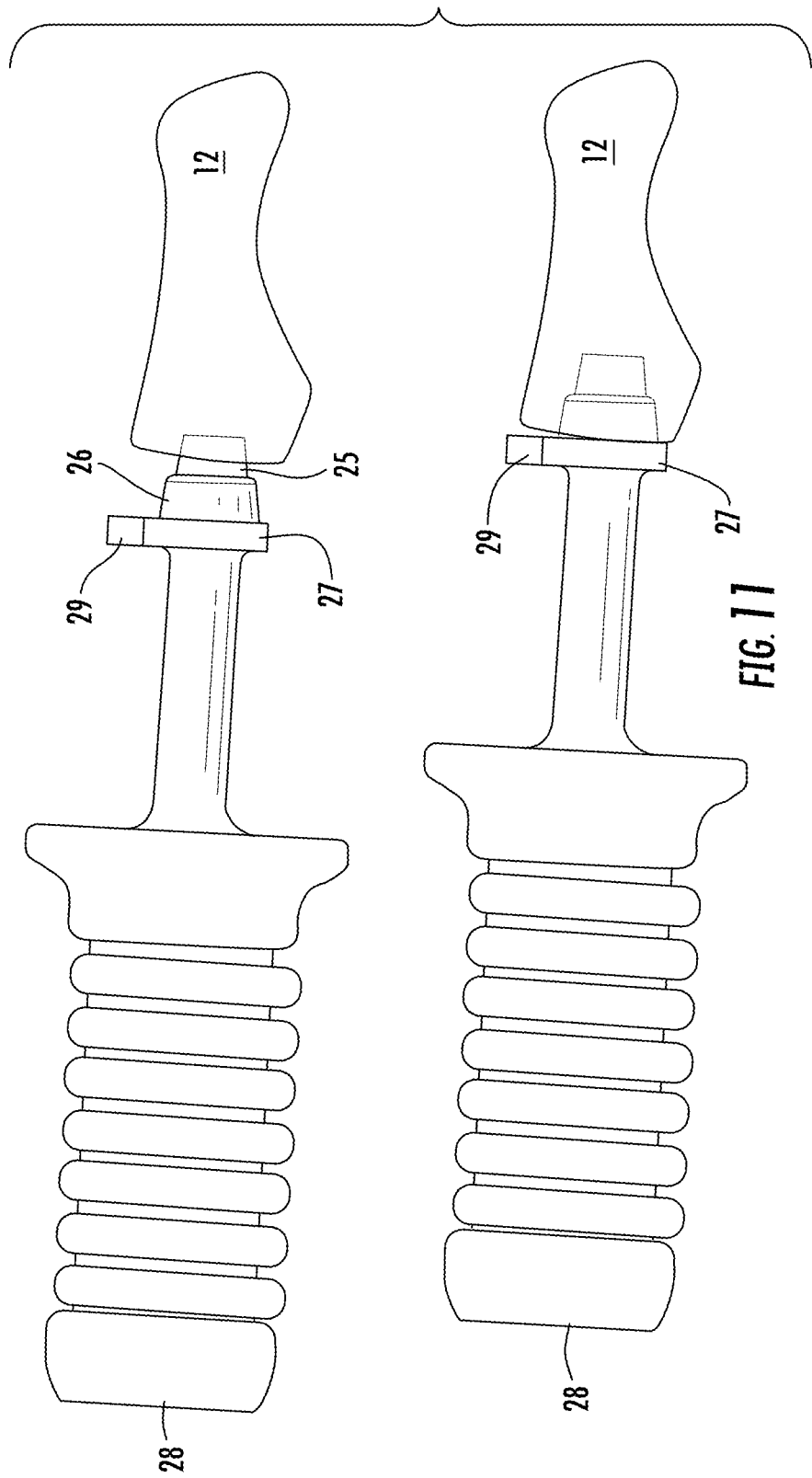
FIG. 11 illustrates distal broaching of the proximal phalanx according to an embodiment of the present invention.

FIG. 10 shows the broach at the guide stage and the final stage of insertion and cutting into the metatarsal bone (11). And FIG. 11 shows the broach at the guide stage and the final stage of insertion and cutting into the proximal phalanx (12).

Figure 19:
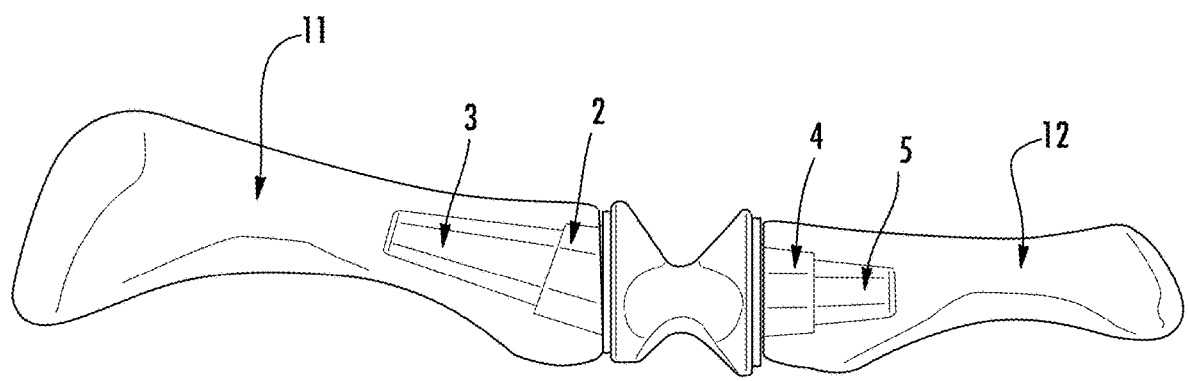
FIG. 19 shows a silicone implant with grommets implanted in place.

FIG. 19 shows an implanted toe implant with proximal grommet (2) in the metatarsal bone (11) and distal grommet (2) in the proximal phalanx (12). FIG. 20 shows the grommet impactor (36), the proximal grommet (2) and the metatarsal bone (11).

Specific embodiments and examples of the methods and instruments described herein are to be understood as illustrative, and many variations can be introduced on these embodiments and examples without departing from the spirit of the disclosure or from the scope of the appended claims. Elements and/or features of different illustrative embodiments and/or examples may be combined with each other and/or substituted for each other within the scope of this disclosure and appended claims.

A first method according to the present invention comprises the following surgical steps:

1) Joint preparation: A longitudinal incision is made over the dorsomedial aspect of the first metatarsophalangeal (MTP) joint. The fascia and medial capsule of the joint are exposed and incised medial to the extensor hallucis longus tendon to prepare a capsuloligamentous flap for later closure and correction of the deviation deformity. If a bursa is present, it is resected. The MTP joint is opened by flexing the toe and incising the dorsal capsular reflections.

2) Bone preparation: The head of the first metatarsal bone is excised distal to the metaphyseal flare at the longest diameter of the metatarsal head. A sagittal saw or other power equipment is used to resect this portion of the head. The bone is preferably resected in ten degrees valgus to conform to normal anatomy. Next, a portion of the proximal phalanx is removed to provide a wider joint. Both of these cuts should be oriented approximately ninety degrees to the floor when patient is in stance. Edges of cut bone are carefully smoothed.

3) Implant sizing: The sizing instrument (6) is positioned against the resected metatarsal bone and the implant size closest to the bone size (without being larger) is chosen. The sizing instrument is provided in separate sterile package. The surgeon is instructed to select the appropriate implant (1) and instrument kit according to the size designated in this step 3). The kit provides all of the instruments necessary to implant the selected size implant.

4) Intramedullary canal preparation: The above described cannulated instrumentation with a single point of reference is used. The proximal wire guide (8) in the designated size is positioned against the resected metatarsal bone (11). The guide wire (10) is driven through the wire guide (8) and up through the intramedullary canal. Previously known techniques do not include use of a wire guide technique.

5) The guide is removed and the cannulated reamer (14) is driven over the guide wire (10), reaming the bone until the depth stop (15) is reached. The reamer (14) and guide wire (10) are then removed. Previously available instrumentation doesn't provide procedure-specific (tapered cannulated) reamers.

6) The guide tip (25) of broach (24) is then inserted into the canal and impacted to cause cutting surfaces of the cutting ring (26) to cut and shape the bone until it reaches its stop (27). The broach has an orientation indicator (29) to correctly align broach (24) during impaction. The cutting ring (26) design enables this broaching step to have minimized bone removal making it easier and more repeatable. The cutting ring (26) cross-section has two flats and two curved sides. Broaching only needs to remove remaining bone after reamers at the corners of the cross-section. Previously available broaches are sized to the silicone stem of the implant. The surgeon was required to finesse the broach, or whatever tools were available, to open the canal just enough to allow the grommet to effectively seat but not too much to prevent a good press-fit. This prior art method of grommet preparation necessitated surgeons who were adept at this free-hand work. The instrument kit of the present invention provides a repeatable press fit for optimal grommet placement without the need for free-hand work.

7) Steps 4)-6) are repeated on the proximal phalanx (12) using the distal wire guide (9), reamer (14) and broach (24). For distal reaming, the reamer depth stop (15) is advanced to the distal stop (18) on the reamer (14).

8) Joint preparation can be checked with trial implants if supplied, or the actual implant if the implants are provided in one package.

9) The grommets are implanted using the grommet placer (30). The implant is then implanted with the stems inserting into the grommets.

10) Range of Motion (ROM) is confirmed and the joint is closed per the surgeon's preferred method.

A second method according to the present invention comprises the following surgical steps:

1) Joint preparation: A longitudinal incision is made over the first MTP joint, just medial to the extensor hallucis longus tendon. The incision is deepened to the joint. A dorsal medial capsulotomy is performed and the joint is dissected free on the dorsal and medial aspects. If desired, the Implant Sizer may be used to estimate the overall width of the osteotomy for the anticipated size implant.

2) Bone preparation: All hypertrophic bone is resected from the first metatarsal head and the base of the proximal phalanx. Using a surgical saw, osteotomies are then performed perpendicular to the weight bearing surface, to enable complete resection of the articular surfaces from the first metatarsal head and base of the proximal phalanx. All resected bone surface are smoothed with a rasp. If desired, the implant sizer may be used to estimate the overall width of the osteotomy for the anticipated size implant.

3) Implant sizing: An implant sizer such as one illustrated in FIG. 15B is positioned against the resected metatarsal bone with the front facing toward the user. The implant size closest to the bone size (without being larger) is chosen. The four sizer "heads" each correspond in thickness, diameter, and overall general shape of the proximal face of the proximal face of the four implant bodies. Placement of the implant sizer above the joint is illustrated in FIG. 15A. This head width approximate the location of the bone resections and provides guidance to the surgeon in determining the proper depth and size of the resection.

4) Optionally, when multiple kits are provided, if a Size 1 or 2 implant is chosen, the corresponding Size 1-2 Instrument Kit is selected and opened. If a Size 3 or 4 implant is chosen, the corresponding Size 3-4 Instrument Kit is selected and opened.

5) Intramedullary canal preparation: The wire guide in the designated size is selected and a labeled end corresponding to proximal end is positioned against the resected metatarsal bone. The guide wire, preferably sized 0.062×4", is driven through the guide and into the intramedullary canal. An example of the wire guide and guide wire, and their positioning against the metatarsal bone, are shown in FIGS. 16A and 16B.

6) The corresponding size cannulated reamer with attached reamer depth guide, also referred to herein as the reamer depth stop, set to the proximal position is driven over the wire, reaming the bone until the reamer depth stop engages the resected metatarsal surface. The reamer and guide wire are then removed. An example of the cannulated reamer and its positioning in the metatarsal bone during the reaming process are shown in FIGS. 17A and 17B.

7) Steps 4) and 5) are repeated for the distal side of the joint in the proximal phalanx. A labeled end of the wire guide corresponding to the distal end is positioned against the resected proximal phalanx bone. The guide wire is driven through the guide and into the intramedullary canal. The reamer depth guide is moved to the distal reamer position for distal reaming using the same reamer. Positioning of the wire guide, reamer and reamer depth stop against the phalanx bone is shown in FIG. 16C. Positioning of the cannulated reamer in the phalanx bone during the reaming process is shown in FIG. 17C.

8) Joint preparation can be checked with a trial implant.

9) Once the sizing has been finalized, the correspondingly sized toe implant with grommets package is selected and opened. Each package may include a label marked with the size and color corresponding to the trial silicone implant for easy identification.

10) The grommets are removed from the tray and placed using the grommet placer instrument. For hard bone, a separate dedicated grommet impactor may be used to fully seat the grommet if necessary. These instruments are used for both proximal and distal grommets. An example of the grommet placer having a grommet placed thereupon, and use of said grommet placer to place a grommet in the metatarstal bone are shown in FIGS. 18A-18C. A grommet impactor is shown in FIG. 20.

11) The sterile silicone implant is then inserted. ROM is confirmed and the joint is closed per the surgeon's preferred method. FIG. 20 shows the silicone implant with grommets implanted in place.

Finally, the combination of any embodiment or feature mentioned herein with one or more of any of the other separately mentioned embodiments or features are contemplated to be within the scope of the instant invention. It should also be noted that each of FIGS. 1-20 are not necessarily to scale.

EXPERIMENTS

Instruments and kits according to the present invention were evaluated by two separate surgical teams:

Experiment 1: Evaluation of Inventive Instruments and Kits in Cadaver Foot by Team 1

Surgical Procedure:
1) One frozen and thawed cadaver foot was used in this evaluation.
2) The joint was prepared by making a longitudinal incision over the first MTP joint, just medial to the extensor halluces longus tendon. The incision was deepened to the joint. A dorsal medial capsulotomy was performed and the joint was dissected free on the dorsal and medial aspects.
3) Bone preparation: Dorsal and medial bone resections were performed to simulate typical bone preparation of an arthritic joint. The sizer instrument was used at this point to estimate the size implant needed by holding it against the dorsal surface of the metatarsal head.
4) Articular surface resection: Using a surgical saw, osteotomies were then performed perpendicular to the weight bearing surface, to enable complete resection of the articular surfaces from the first metatarsal head and base of the proximal phalanx.
5) Implant sizing: The sizing wheel was positioned against the resected metatarsal bone and the implant size closest to the bone size (without being larger) was chosen. For investigation purposes a Size 2 was chosen in order to use both sets of instruments (the Size 1-2 Kit and the Size 3-4 Kit). However, a Size 3 was the best selection for this anatomy.
6) Intramedullary canal preparation: Cannulated instrumentation with a single point of reference. The wire guide in the designated size was selected and the end labeled "PROX" (see FIG. 16A) was positioned against the resected metatarsal bone. A 0.062" guide wire was driven through the wire guide and up through the intramedullary canal.
7) The wire guide was removed and the corresponding size cannulated reamer with attached reamer depth stop set to the proximal position was driven over the wire, reaming the bone until the reamer depth stop engages the resected metatarsal surface. The reamer depth stop worked well at limiting the travel of the reamer. The reamer and guide wire were then removed.
8) Next the wire guide end labeled "DIST" (see FIG. 16A) was positioned against the resected proximal phalanx bone. The 0.062" guide wire was driven through the wire guide and up through the intramedullary canal.
9) The guide was removed and next reaming was performed. For distal reaming, the depth stop was advanced forward to the distal groove on the reamer. The reamer depth stop worked well at limiting the travel of the reamer. The reamer and guide wire were then removed.
10) The proximal and distal grommets were inserted using the grommet placer instrument. The proximal grommet was picked up out of the tray with the distal end of the placer and inserted into the reamed hole. A mallet was used to impact the placer until the grommet was seated into the metatarsal bone. The placer was rotated during impaction so that the placer could impact all locations of the grommet. The plantar edge of the grommet was difficult to fully seat. The placer was removed and the mallet impacting on the grommet directly was effective to fully seat the grommet.

11) Due to the soft bone in the proximal phalanx, the distal grommet was easily seated with pressure using the grommet placer.

12) The Size 1 and 2 implants were inserted into the grommets and ROM was assessed. Because these implants were smaller than the joint size, dorsal bone blocking occurred which limited full dorsiflexion.

13) The Size 3-4 reamer was then used to prepare the bones for the Size 3-4 grommets. The Size 3-4 grommets were then impacted with the grommet placer. Again, for the proximal grommet, full seating was accomplished by removing the placer and impacting with the mallet directly on the area to be seated. Full seating was accomplished without broaching.

14) The Size 3 and 4 implants were both inserted and ROM was assessed. Full range was performed without dorsal bone contact or impingement occurring.

DISCUSSION/CONCLUSION

Team 1 determined that the instruments work well to prepare the joint and insert the grommet and implant. Broaching was not necessary to seat the grommets. Team 1 further suggested adding a bone resection estimate to the sizing instrument similar to that shown in FIGS. 15A and 15B, as well as changing the size/shape of the grommet stops (32) on the grommet placer (30) from the design shown in FIG. 12A to the design as shown in FIG. 18A. An Impactor instrument such as that shown in FIG. 20 was also suggested.

Experiment 2: Evaluation of Inventive Instruments and Kits in Cadaver Foot by Team 2

Test Equipment:
One frozen/thawed cadaveric foot and standard hospital power equipment.

Surgical Procedure:
1) One cadaver foot, male, was used in this evaluation.
2) The joint was prepared by making a longitudinal incision over the first MTP joint, just medial to the extensor halluces longus tendon. The incision was deepened to the joint. A dorsal medial capsulotomy was performed and the joint was dissected free on the dorsal and medial aspects.
3) Implant sizing: The sizing wheel was positioned against the dorsal surface of the metatarsal bone and the implant size closest to the bone size (without being larger), i.e., Size 3 was chosen.
4) The Size 3 sizing wheel, a sizing instrument used in this experiment, was positioned over the joint to estimate the amount of bone resection. A surgical marking pen was used to indicate the resection lines.
5) Articular surface resection: Using a surgical saw, osteotomies were performed perpendicular to the weight bearing surface, to enable complete resection of the articular surface from the first metatarsal head and base of the proximal phalanx. After the resections, the sizer head Size 3 was placed in the space to confirm sizing.
6) Intramedullary canal preparation: Cannulated instrumentation with a single point of reference. Both the reamer reference guide and the wire guide instruments were shown and explained to the surgical team, which chose to use the wire guide because it was thought to give a more accurate placement. The wire guide in the designated size was selected and the end labeled "PROX" (see FIG. 16A) was positioned against the resected metatarsal bone. The 0.062" guide wire was driven through the guide and up through the intramedullary canal.
7) The wire guide was removed from the guide wire. The corresponding size cannulate reamer with attached reamer depth stop set to the proximal position was driven over the guide wire, reaming the bone until the reamer depth stop engages the resected metatarsal surface. The reamer depth stop worked well at limiting the travel of the reamer. The reamer and guide wire were then removed.
8) Next the wire guide end labeled "DIST" (see FIG. 16A) was positioned against the resected proximal phalanx bone. The 0.062" guide wire was driven through the guide and up through the intramedullary canal.
9) The guide was removed and next reaming was performed. For distal reaming, the reamer depth stop was advanced forward to the distal groove on the reamer. The reamer depth stop worked well at limiting the travel of the reamer. The reamer and guide wire were then removed.
10) The proximal and distal grommets were inserted using the grommet placer instrument. The proximal grommet was picked up out of the tray with the distal end of the placer and inserted into the reamed hole. A mallet was used to impact the placer until the grommet was seated into the metatarsal bone. The placer was rotated during impaction so that the placer could impact all locations of the grommet. The grommet was not fully seated with just the grommet placer. The impactor instrument was used to fully seat both grommets.
11) The Size 3 implant was inserted into the grommets and ROM was assessed.

DISCUSSION/CONCLUSION

Team 2 determined that broaching was not necessary to seat the grommets. The impactor was determined to be useful for firmly seating the grommets. Otherwise instruments were effective at preparing the bones and inserting the grommets and implant.

What is claimed is:
1. A kit for use in joint implant surgery, comprising:
a reamer comprising:
a reamer shaft comprising a proximal end and a distal end;
a cutting tip located at the distal end of the reamer shaft;
a hollow channel within and extending through the cutting tip and the reamer shaft configured to receive a guide wire, and at least two grooves located on the reamer shaft, representing a proximal stop position and a distal stop position wherein at least two flexible tongs are configured to snap in place at the proximal stop position and then the distal stop position when a reamer depth stop is slid on to the reamer in a direction from the proximal end to the distal end;
wherein spring action enables the reamer depth stop to click into place in the proximal stop position or the distal stop position;
wherein each of the at least two flexible tongs comprise a shape configured to:
discourage slippage out of the proximal stop position and the distal stop position when pushed toward the proximal end of the reamer; and allow release from the proximal stop position and the distal stop position when the reamer stop is pushed towards the distal tip of the reamer;

the reamer comprising an indent and a flattened portion located near the proximal end of the reamer, said indent and flattened portion configured and shaped to facilitate quick connect attachment to a driving tool;

a grommet placer instrument, comprising:

a grommet placer shaft comprising a proximal end and a distal end;

a grommet placer head located on the proximal end of the grommet placer shaft; and at least two flexible split shafts located on the distal end of the grommet placer shaft;

a wire guide, comprising a wire guide body, a proximal guide located on a first end of the wire guide body, and a distal guide located on a second end of the wire guide body, wherein the first and second ends are opposite ends of the wire guide body;

a broach comprising a guide tip and a cutting ring provided adjacent a broach stop;

the broach comprising a site guide that indicates an orientation, so as to maintain orientation of the broach during impaction;

wherein the broach stop is configured to stop the cutting ring;

wherein the guide wire comprises an elongated guide wire body and a needle head located on one end of the elongated guide wire body; and a sizing instrument provided in a separate sterile package.

2. The kit of claim 1, further comprising a joint implant, wherein the joint implant is provided in a separate sterile package.

3. The kit of claim 1, further comprising a grommet impactor.

4. The kit of claim 1, further comprising a grommet clip extending from each of the at least two flexible split shafts.

5. The kit of claim 4, wherein one or more grommet stops are shaped and configured to prevent a grommet placed on the grommet placer instrument from sliding proximally on the grommet placer shaft; and wherein the grommet clips are shaped and configured to prevent the grommet from falling off tips of the grommet placer.

* * * * *